United States Patent
McBride et al.

(10) Patent No.: US 6,576,746 B2
(45) Date of Patent: *Jun. 10, 2003

(54) SITE-SPECIFIC LABELING OF DISULFIDE-CONTAINING TARGETING VECTORS

(75) Inventors: William J. McBride, Summit, NJ (US); Gary L. Griffiths, Morristown, NJ (US)

(73) Assignee: Immunomedics, Inc., Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 59 days.

(21) Appl. No.: 09/417,109

(22) Filed: Oct. 13, 1999

(65) Prior Publication Data

US 2003/0092198 A1 May 15, 2003

Related U.S. Application Data

(60) Provisional application No. 60/103,904, filed on Oct. 13, 1998.

(51) Int. Cl.$^7$ .................... C07K 16/00; A61K 51/00; G01N 33/48; A61B 5/055
(52) U.S. Cl. ............ 530/404; 530/389.1; 530/389.8; 530/391.1; 530/391.5; 530/391.7; 530/402; 530/408; 424/1.11; 424/1.65; 424/1.69; 424/9.3; 424/9.322; 424/9.351; 424/193.1; 424/194.1; 436/63; 436/504; 436/512; 435/7.9; 435/188; 435/810
(58) Field of Search ................ 530/404, 389.1, 530/389.8, 391.3, 391.5, 391.7, 402, 408; 424/1.11, 1.65, 1.69, 9.3, 9.322, 9.351, 193.1, 194.1; 436/63, 504, 512; 435/7–9, 188, 810

(56) References Cited

U.S. PATENT DOCUMENTS 5,057,313 A * 10/1991 Shih et al. ............... 424/85.91
5,156,840 A * 10/1992 Goers et al. ............. 424/85.91
5,746,996 A * 5/1998 Govindan et al. ......... 424/1.69

FOREIGN PATENT DOCUMENTS

WO        96/40289      12/1996

OTHER PUBLICATIONS

Bridger et al., *Bioconjugate Chemistry*, vol. 7, No. 2, pp. 255–264, 1966.*
Zara et al.; "A Carbohydrate–Directed Heterobifunctional Cross–Linking Reagent for the Synthesis of Immunoconjugates[1]"; Anal. Biochemical; vol. 194; 1991; pp. 156–162; XP–000872283.
Bridger et al.; "Comparison of Cleavable and Noncleavable Hydrazinopyridine Linkers for the $^{99m}$Tc Labeling of Fab' Monoclonal Antibody Fragments"; Bioconjugate Chemistry; vol. 7, No. 2; 1996 pp. 255–264; XP–000558423.

* cited by examiner

Primary Examiner—Christopher S. F. Low
Assistant Examiner—Abdel A. Mohamed
(74) Attorney, Agent, or Firm—Foley:Lardner

(57) ABSTRACT

A method of producing a diagnostic or therapeutic conjugate of a protein, polypeptide or peptide containing at least one disulfide bond which is necessary to maintain its biological activity, and bearing at least one thiol-containing moiety linked thereto through a hydrazone or hydrazine linkage, is effected by contacting said protein, polypeptide or peptide with a thiol-reactive diagnostic or therapeutic agent, either preformed or generated in situ, to form a stable diagnostic or therapeutic conjugate of the protein, polypeptide or peptide without substantial cleavage of the disulfide bond. Diagnostic and therapeutic conjugates produced using the foregoing method, as well as kits for carrying out the method are provided.

25 Claims, No Drawings

SITE-SPECIFIC LABELING OF DISULFIDE-CONTAINING TARGETING VECTORS

This application claims benefit of provisional application Ser. No. 60,103,904 filed Oct. 13, 1998.

BACKGROUND OF THE INVENTION

1. Field of the Invention

This invention relates to methods for introducing thiol-containing linkers onto disease targeting agents that contain disulfide bonds, the radiolabeled targeting agents and drug conjugates produced using these methods, and use of the radiolabeled or drug-bearing targeting agents for diagnosis and treatment.

2. Description of Related Art

Free thiols offer a unique chemical handle for the attachment of numerous species to specific targeting agents, because of the specificity of the thiol group for reactive groups such as haloacetates, maleimides, and activated sulfonyl groups, and for reduced metal species such as reduced pertechenetate and perrhenate, and certain other thiophilic metals such as zinc, copper, mercury, cadmium, platinum, palladium, lead and bismuth. However, a complicating issue with many proteins, polypeptides and peptides is the presence of disulfide bonds that are critical to their structural integrity. The inherent reactivity of the thiol group can lead to breakage of such disulfide bonds, with possible formation of mixed disulfides, and an inability of the proteins, polypeptides and peptides to bind to their target antigen or receptor.

Antibody fragments, as well as sub-Fab' fragments, single-chain antibodies, diabodies, polypeptides and peptides, offer advantages for in-vivo targeting of radioimaging and radio-therapeutic isotopes and drugs because the smaller fragments will target and clear faster than an intact IgG or larger protein. For example, a radiolabeled antibody fragment delivers a dose of a therapeutic or imaging isotope to a target more quickly than intact IgG and the faster clearance will minimize the radiometric dose to the non-target tissues. Rapid targeting is especially important for isotopes with short half-lives such as Tc-99m (t½=6 hr) or Re-188 (t½=17 hr). Tc and Re cations bind strongly to thiol-containing ligands but conjugation of these ligands to antibodies or antibody fragments can present some difficulties.

A divalent antibody fragment such as a F(ab')$_2$ fragment should have increased total targeting compared to a Fab' fragment because the divalent binding region will increase the affinity of the protein for the antigen. F(ab')$_2$ fragments are made up of two Fab' fragments joined by one or more disulfide bonds, which are sensitive to reduction by free thiols both during and after the conjugation of a thiol-containing moiety. Thus, it is necessary to conjugate a thiol-containing ligand to the protein either using a protected thiol which is subsequently deprotected, or using a low thiol concentration and hydrophilic thiols to minimize the interaction of the free thiols on the ligand with the disulfides on the antibody.

Another problem that can occur during conjugation to a non-specific site on a targeting agent is that the conjugate may be bound to or near the antigen-binding region of an antibody or the receptor-binding region of a peptide/polypeptide, which can reduce or eliminate the binding affinity of the antibody or peptide for the antigen or receptor. The conjugation of haptens to periodate-oxidized carbohydrate sites (aldehydes and ketones) is one method of site-specifically forming conjugates. The carbohydrate regions can be genetically engineered into specific sites on proteins or peptides so, for example, it is possible to place a carbohydrate at a site on a F(ab')$_2$ fragment that will not interfere with the binding of the antibody fragment to the antigen.

The presence of carbohydrate residues on the light chains of certain IgGs has been established. Such residues remain on F(ab')$_{2S}$ and F(ab)$_{2S}$ after pepsin or papain digestion, respectively. As such, they represent a masked potential site-specific chemical handle for haptenic attachment. In addition, certain murine antibodies have been reengineered to produce humanized complementarity determining region versions of the same antibodies, while simultaneously engineering glycosylation sites at positions remote to the antibody's antigen-binding site. This enables the insertion of carbohydrate at desired positions within the protein, including insertion of carbohydrate in the CH$_1$ domain and the variable region on either light or heavy chains.

It is also necessary to have a conjugate which is sufficiently stable in-vitro, and in-vivo so that the biodistribution of the radiolabel reflects the biodistribution of the antibody fragment. If the linkage of the conjugate to the antibody or the attachment of the radioisotope to the conjugate is unstable then there may be a substantial reduction of radioisotope that reaches the target. The radioisotope that separates from the protein may contribute to the background activity, which would further obscure targeting.

A continuing need exists to prepare thiol-containing disulfide-linked targeting vectors which can be, readily radiolabeled with thiophilic metal ions for use in radioimaging and radiotherapy, or substituted with drugs for targeted chemotherapy. Such an invention must successfully address the multiple problems discussed above.

SUMMARY OF THE INVENTION

One object of the present invention is to provide conjugates of disulfide-containing targeting proteins, polypeptides and peptides, e.g., divalent antibody fragments and (SV)$_{2S}$, with thiol-containing ligands without cleaving the disulfide bonds of the targeting proteins.

Another object of the invention is to use the substituted thiol group attached to the disulfide-containing proteins or peptides as a specific chemical handle to further attach certain radioisotopes or chemotherapy agents.

Another object of the invention is to provide radiolabeled proteins that are stable in vitro and in vivo.

Yet another object is to provide methods for the use of stably substituted disulfide-containing proteins, polypeptides and peptides for radiodiagnosis, radiotherapy and chemotherapy of disease.

These and other objects are achieved by providing a method of producing a diagnostic or therapeutic conjugate of a protein, polypeptide or peptide containing at least one disulfide bond which is necessary to maintain its biological activity, and bearing at least one thiol-containing moiety linked thereto through a hydrazone or hydrazine linkage, comprising contacting the protein, polypeptide or peptide with a thiol-reactive diagnostic or therapeutic agent, either preformed or generated in situ, to form a stable diagnostic or therapeutic conjugate of the protein, polypeptide or peptide without substantial cleavage of the disulfide bond.

In the foregoing method, the thiol-containing moiety linked to the protein, polypeptide or peptide through a hydrazone or hydrazine linkage is joined by reacting the disulfide bond-containing protein, polypeptide or peptide which also contains an aldehyde or ketone group with a thiol-hydrazine of the formula HS-Q-NHNH$_2$, wherein Q is a linking moiety selected from the group consisting of alkyl groups, aryl groups, cycloalkyl groups, peptides, and combinations thereof; and optionally reducing the resultant hydrazone to a hydrazine.

The diagnostic or therapeutic agent in the conjugate can be a thiol-binding cationic. radioisotope or a drug derivative comprising a thiol-binding linker.

In one preferred embodiment, the protein is a glycosylated divalent antibody fragment whose partially oxidized carbohydrate portion is joined through the hydrazone or hydrazine linkage to the thiol-containing moiety.

Preformed, stable kits for effecting radiolabeling according to the foregoing method also are provided.

DETAILED DESCRIPTION

The present inventors have developed a method for conjugating a thiol-containing peptide linker or ligand to a disulfide-containing protein or peptide, e.g., a F(ab')$_2$, through a carbonyl function, e.g., a periodate oxidized carbohydrate portion of the protein, without reducing disulfide bonds that maintain structure and/or conformation related to activity, e.g., reduction of a F(ab')$_2$ fragment to Fab' during the conjugation or labeling process. Conjugates have been produced in which the attachment of the linker or ligand to the disulfide bond-containing protein is stable and the attachment of a radiolabel, e.g., Tc-99m, to the ligand is stable in vitro and in vivo. In the case of a glycosylated F(ab')$_2$ fragment, preferred embodiments of Tc-99m-labeled peptide chelators delivered a higher percentage of the injected dose to a tumor than I-125-labeled F(ab')$_2$ or Tc-99m-labeled Fab'.

Surprisingly, the present inventors have found that the acyl hydrazides commonly used for the conjugation of drug and chelate-nuclide molecules to antibodies through oxidized carbohydrate moieties are very unstable, even in-vitro. This was shown in stability experiments with the Tc-99m radiolabeled conjugates IMP 126-LL2-F(ab')$_2$ and IMP 140-LL2-F(ab')$_2$. LL2 is an anti-CD-22 monoclonal antibody (mab) that is described in U.S. Pat. No. 5,789,554.

IMP 126 Ac-D-Lys(TscG-Cys-)-D-Asp-D-Ala-Gly-NHNH$_2$

IMP 140 Ac-D-Asp-Lys(TscG-Cys-)-D-Asp-D-Lys-D-Asp-NHNH$_2$

TscG stands for H$_2$NCSNHN=CHC(O)— thiosemicarbazonylglyoxyl

The Tc-99m labeled peptide would dissociate from the protein when stored in solution over time. The in-vitro loss of the labeled peptide was monitored by size exclusion HPLC and reverse phase HPLC. The stability of the acyl hydrazide connection could be controlled to some extent by changing the amino acids adjacent to the acyl hydrazide. The peptide IMP 126 formed a more stable (though still unstable) connection to the LL2 F(ab')$_2$ than IMP-140: possibly the aspartic acid residue catalyzed the dissociation of the labeled peptide.

It is possible to stabilize the peptide linker-to protein linkage by using a hydrazine (e.g. IMP 155) rather than an acyl hydrazide for the reaction with the carbonyl function e.g., oxidized carbohydrate. There was no detectable loss of labeled peptide after in-vitro incubation overnight.

IMP 155 H$_2$NHN-CH$_2$-CO-D-Asp-D-Lys(TscG-Cys-)-D-Asp-D-Lys-NH$_2$

Surprisingly the free thiol-containing peptide could be conjugated without appreciable reduction of the hinge region disulfide.

A consistent peptide loading was observed (about 3.8–4.3 peptides/LL2 F(ab')$_2$ fragment) over a range of peptide/antibody ratios (100:1, 50:1, 10:1) used for the conjugation.

The antibody conjugate could be formulated into a single vial kit and labeled with Tc-99m at room temperature.

The Tc-99m labeled conjugate was labeled site-specifically on the peptide attached to the oxidized carbohydrate. This was shown first in control experiments in which the LL2 F(ab')$_2$ was put through the conjugation process except that no periodate was added during the oxidation step. The control was a treated with Tc-99m-glucoheptonate and formed only 6% Tc-99m-labeled protein as measured by ITLC whereas the IMP 155-LL2 F(ab')$_2$ labeled under the same conditions afforded substantial quantities of the labeled antibody fragment (70–80%). The other proof that the Tc-99m is attached to the peptide is that the labeled acylhydrazide peptides, which used the same Tc-99m ligand as IMP 155, had the activity dissociated from the protein as the Tc-99m labeled peptide, as shown by size exclusion and reverse phase HPLC analysis. The proof that the peptide is attached to the oxidized carbohydrate is that the conjugation with the periodate oxidized LL2 F(ab')$_2$ produces a protein which contains free thiols (2–3 thiols/LL2 F(ab')$_2$ measured by UV) and conjugation with the unoxidized antibody produces a protein which contains no free thiols.

The Tc-99m labeled IMP 155-LL2 F(ab')$_2$ conjugate was stable in-vitro, and in-vivo.

The Tc-99m labeled antibody showed tumor targeting at 24 hr in Ramos tumor-bearing mice (see Example 3 and 4 below). The divalent antibody fragment delivered a higher dose to the tumor than the iodinated LL2-F(ab')$_2$or the Tc-99m-Fab'.

The foregoing experimental results demonstrate that the present methods permit the introduction of a thiol ligand-bearing peptide with a stable linkage site-specifically to the oxidized carbohydrate portion of an antibody or antibody fragment. This method can be applied to any aldehyde or ketone-containing protein, polypeptide or peptide. The conventional methods introduce a protected thiol which must subsequently be deprotected to produce the free thiol. These linkers are often attached to the oxidized carbohydrate groups through acyl hydrazides which have been found to be an unstable linkage. The free thiol conjugates that have been made by the present method can be used to form conjugates to other moieties such as drugs, antibodies, antibody fragments, proteins, glycoproteins, DNA, RNA, PNA, metal complexes, radiolabeled species (imaging and therapy), enzymes, toxins and sugars.

Such fragment-present carbohydrate can be used to attach haptens such as thiol-containing chelators which can be radiolabeled subsequently with thiol-binding radiometals. Carbohydrate containing vicinal diols can be oxidized to produce aldehyde and ketone functions with an agent such as periodate, and mixed with a thiol-containing hydrazine-containing hapten, generally represented as HS-Q-NHNH$_2$, to effect conjugation. Optionally, the formed hydrazones linking the hapten to the protein carbohydrate can be reduced with a reductant such as sodium cyanoborohydride to produce a thiol-hapten conjugate without compromising hinge-region disulfide bonds.

The thiol-containing hydrazine-containing moiety HS-Q-NHNH$_2$ can have a wide range of structures. The group, Q, can include: alkylene groups, including straight or branched chain C$_{2-30}$ alkylene groups; C$_{5-8}$ cycloalkylene groups; C$_{6-30}$ fused or linked aryl groups, optionally incorporating from one to eight heteroatoms in one or more of the aromatic rings, including but not limited to phenylene, naphthylene, furylene, benzofurylene, pyridylene, purinylene, piperidylene, and the like; peptides and/or peptidyl mimetics of one to 20 amino acids or amino acid analogs in length, preferably wherein one or more of the amino acids is cysteine, for its thiol function, and a terminal serine or threonine, oxidized to an aldehyde, reacted with hydrazine and reduced to form the hydrazinyl substituent. Combinations of the foregoing structural components also can be used to construct the group, Q. Furthermore, the foregoing components can bear one or more substituents that do not interfere with the conjugation reactions, including but not limited to halogens, hydroxyl or alkoxyl groups, including protected hydroxyl groups, carboxyls and carboxylic ester groups, alkyl groups, cyano groups, primary, secondary and tertiary amino groups, including protected amino groups, amides, urethanes, ureas, nitro groups, and the like. The peptides disclosed herein are examples of peptides suitable for this purpose.

The structures represented by Q can be readily synthesized by conventional methods. Many aliphatic and aromatic single, multiple or fused ring compounds are commercially available, with substituents suitable or adaptable for further elaboration. Ring compounds bearing one or two carbonyl compounds, e.g., aldehydes, ketones, carboxylic acids or esters, and amides can be found in reagent catalogues. Other substituents such as hydroxyls, haloalkyl groups, hydroxyls, amines, cyano groups, isocyanates, and the like can be used as such or transformed into handles for further elaboration. Small linker synthons such as glyoxyl esters, sugar derivatives, alpha-halo acyl compounds, e.g., alpha-bromoacetyl esters, acid chlorides, are useful for introducing free or masked carbonyl groups for reaction with hydrazine, followed by reduction with, e.g., sodium cyanoborohydride, to produce the hydrazine function of $HS-Q-NHNH_2$ or for introducing alkyl halide groups for reaction with sodium sulfide or hydrosulfide to produce the thiol function of $HS-Q-NHNH_2$. Peptides can introduce the thiol function by incorporation of cysteines.

Methods of introducing nascent aldehyde and ketone residues into targeting vectors using standard methods of molecular biology may also be used. For instance, a polypeptide can be constructed with an N-terminal serine or threonine moiety, which can then be specifically oxidized to generate N-terminal carbonyl groups. Such derivatives then constitute specific chemical 'handles' for the attachment of thiol-containing haptens.

Preferred ligand-bearing peptides, such as IMP 155, are advantageous because they contain a hydrazine, several hydrophilic D-amino acids and a metal binding ligand. The hydrazine is used to form a hydrazone linkage to aldehydes or ketones on the oxidized portion of the carbohydrate groups on a glycosylated antibody or antibody fragment. The ligand forms a stable Tc(V) oxo complex with the diagnostic imaging isotope Tc-99m. Without wishing to be bound by any theory, it appears that the hydrophilic amino acids make the peptide sufficiently hydrophilic so that disulfide interchange or mixed disulfide formation is minimized during the conjugation of the free thiol-containing peptide to the antibody. The hydrophilic nature of the peptide should keep the conjugated peptide at the surface of the protein where it can react with the Tc-99m when it is added. In a preferred embodiment, D-amino acids are used to minimize metabolism of the metal-complexed peptide after injection. This is done so that, in the event the protein is degraded, the hydrophilic metal-containing peptide will not be metabolized and, because it is hydrophilic, any labeled peptide which escapes the cell will be rapidly renally excreted.

EXAMPLES

The following examples are illustrative of the methods and compositions of the invention but are not limitative. The ordinary skilled artisan will appreciate that many other peptides, antibody fragments and ligands may be used in place of those illustrated while still remaining within the scope of the invention.

Example 1

Preparation of Labeled F(ab')$_2$
$N^\alpha$-Boc-$N^\beta$-Boc-Hydrazinoacetic Acid A 500 mL Parr bottle was charged with 18.00 g (1.96× $10^{-1}$ mol) glyoxylic acid monohydrate, 25.84 g (1.95×$10^{-1}$ mol) t-butylcarbazate, 0.72 g 10% palladium on carbon, 100 mL methanol, 50 mL dioxane and then placed on a Parr hydrogenation apparatus under an atmosphere of hydrogen (50 PSI). The reaction mixture was shaken at room temperature and the hydrogen pressure was adjusted several times to maintain the pressure at 50 PSI. A precipitate formed as the reaction proceeded. The reaction was stopped after 3 hr and an additional 100 mL of methanol was added to the reaction mixture which was then placed under 50 PSI hydrogen and shaken for 21 hr. The contents of the Parr bottle were dissolved: in 400 mL methanol and filtered through celite. The filtrate was concentrated under vacuum on the rotary evaporator to afford 36.4 g (98.1%) of a white solid product. This crude product 14.0 g (7.37×$10^{-1}$ mol) was dissolved in a solution containing 130 mL dioxane and 80 mL 1 M NaOH and cooled in an ice bath. Di-t-butyl dicarbonate, 17.76 g (8.14×$10^{-1}$ mol, 110 M%) was added and the solution was allowed to slowly warm to room temperature and stir for 18 hr. The contents of the reaction were concentrated under reduced pressure on the rotary evaporator and mixed with 150 mL 1 M citric acid. The mixture was then extracted with 2×150 mL portions of ethyl acetate. The organic extracts were combined, washed with 100 mL saturated sodium chloride solution, dried over sodium sulfate, filtered and concentrated in vacuo to obtain 21.0 g (98%) of the product as an oil which slowly crystallized.

Peptide Synthesis

Peptide IMP 155 ($H_2NHN-CH_2-CO-D-Asp-D-Lys(TscG-Cys-)-D-Asp-D-Lys-NH_2$) was synthesized by Fmoc based solid phase synthesis on an Advanced ChemTech, 348 multiple peptide synthesizer. The peptides were synthesized using Rink amide resin on a 0.05 mmol/well scale (48 well synthesis block). The repetitive coupling process is as follows:

Fmoc Cleavage

The resin is vortex mixed for 4 min with 1.5 mL of 25% piperidine in DMF. The block is then drained and the resin is Vortex mixed for 15 min with 1.5 mL of 25% piperidine in DMF.

Post Fmoc Cleavage Wash

The resin is washed with 1.5 mL portions of NMP, isopropanol, NMP, isopropanol, and 4 NMP washes. The resin is vortex mixed with each of the washing solutions for at least one minute before the liquid is drained.

Coupling

The protected amino acid is dissolved in NMP (0.5 M) which contains 0.5 M HOBt. The system fluid, NMP (300 µL) is added to the resin followed by the addition of diisopropylcarbodiimide solution (600 µL, 0.5 M in NMP, 6 equivalents) and 600 µL of the amino acid solution (6 equivalents relative to the resin). The mixture is vortex mixed for 1 hr at room temperature and then washed as described above. The entire process is repeated for the addition of each amino acid.

IMP 155

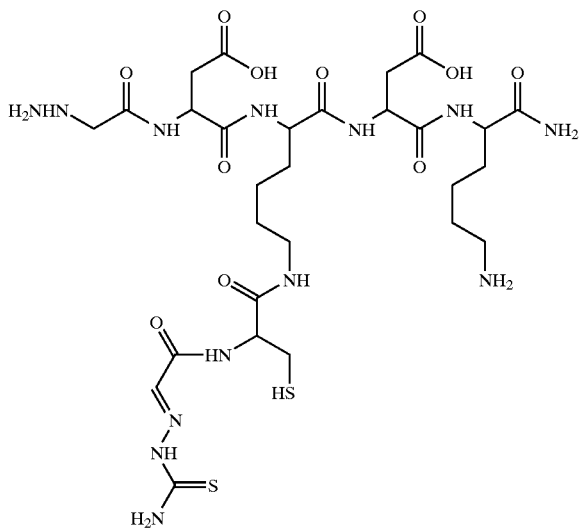

Periodate Oxidation of LL2 F(ab')$_2$

The carbohydrate portion of murine LL2 F(ab')$_2$ (4 mg/mL) was oxidized with 15 mM NaIO$_4$ at 0° C. for 1 hr in the dark at pH 5.3. A glycerol/water solution (1:1) was then added (50 μL for 2.5 mL antibody solution) and the solution was incubated for 15 mm at 0° C. in the dark. The oxidized antibody was then purified through a Sephadex G 50–80 spin column in pH 5.3 acetate buffered saline (ABS, 50 mM acetate).

Conjugation Conditions

The peptide, IMP 155, was conjugated to the periodate oxidized LL2 F(ab')$_2$ fragment (4 mg/mL, LL2 F(ab')$_2$) in a molar ratio of 100:1 peptide/antibody at pH 5.3 in acetate buffered saline for 2 hr at room temperature by adding the antibody solution to the appropriate amount of peptide in a septum sealed evacuated vial. The conjugated antibody fragment was purified twice through Sephadex G 50–80 gel spin columns (pH 5.3 ABS) to remove the unbound excess peptide at the end of the conjugation time. Analysis of the conjugate by MALDI mass spectroscopy showed that an average of four peptides were conjugated per antibody fragment.

| Sample | MALDI Data MH+ |
|---|---|
| LL2 F(ab')$_2$ | 103514 |
| Oxidized LL2 F(ab')$_2$ | 103168 |
| IMP 155-LL2 F(ab')$_2$ Conjugate | 106240 |

Solutions Used for Kit Preparation

αD-Glucoheptonate/Acetate Buffer

A buffer solution was prepared by making a solution which contained 200 mM α-D-glucoheptonic acid sodium salt and 21 mM sodium acetate at pH 5.3. This solution was diluted in half with water to give a 100/10.5 mM (glucoheptonate/acetate) solution used for the kit formulation.

SnCl$_2$

A bulk SnCl$_2$ solution was prepared by dissolving tin metal in 6 M HCl at a concentration of 200 mg/mL; A 2 mg/mL solution of stannous was prepared by diluting an aliquot of the 200 mg/mL stannous solution 100 fold in the glucoheptonate buffer.

Sucrose Solution

A 1 M sucrose solution was prepared for addition to the kits.

Kit Formulation

The purified conjugate solution was passed through a pH 7.3, 0.1 M phosphate buffered Sephadex G 50–80 gel spin column (A mg/mL LL2 F(ab')$_2$. The conjugate, 1 mg, (250 μL) was mixed with 12.5 Mg SnCl (6.25 μL), 446 Hg α-D-glucoheptonic acid sodium salt, (11.7 μL of glucoheptonate buffer+the buffer in the stannous solution), and 19 mg sucrose (55.6 μL) in a total volume of approximately 0.3 mL. The mixture was frozen immediately, lyophilized and septum sealed under vacuum.

Kit Labeling Conditions

The contents of the kit were dissolved in 0.4 mL saline and the solution was allowed to stand for 5 min before the addition of Na99m-TcO$_4$ in saline (0.4 mL). The kit solution was incubated for 30 mm at room temperature before use. HPLC analysis on a Bio-Sil size exclusion column indicated that 96% of the activity was attached to the protein and 4% of the activity was present as small molecular weight material.

Example 2

In-vivo Stability of TC-99m Labeled IMP 155-LL2 F(ab')$_2$ Conjugate, Biodistribution and Serum Analysis in BALB/c Mice Tc-99m Labeling & Purification The LL2-F(ab')$_2$ conjugate was labeled at room temperature by exchange with Tc-99m glucoheptonate as follows:

A GLUCOSCAN™ (DuPont) glucoheptonate labeling kit was labeled with 30 mCi Tc-99m in 2 mL. The Tc-99m glucoheptonate 0.6 mL was added to the IMP 155-LL2-F(ab')$_2$ conjugate kit vial (containing 1 mg conjugate, and sucrose) prepared as described in Example 1. The vial was incubated at room temperature for 30 min. The labeled material was then purified through two successive 3-mL Sephadex G 50–80 spin columns (pH 7.3, 0.1 M PBS). The product was diluted with saline to 5 mCi/mL in an empty sterile vial.

Biodistribution Study

Nine BALB/c mice were injected with 100 μL (500 μCi) of the purified Tc-99m-LL2 F(ab')$_2$ conjugate. The animals were anesthetized and sacrificed, 3 animals per time point, at 1 hr, 4 hr, and 24 hr. Serum for analysis was also collected at 1 hr, 4 hr and 24 hr. The serum samples were frozen after isolation and thawed just before HPLC analysis on the size exclusion HPLC column (Bio-Sil SEC 250, Gel-filtration HPLC Column, 300 mm×7.8 mm). The following tissues and organs were collected and counted: Blood, Liver, Kidneys, Spleen, Lungs, Stomach, Small Intestine, Large Intestine, Muscle, Urine.

HPLC analysis of the serum samples indicated that the activity in the serum was present primarily Tc-99m-IMP 155-LL2 F(ab')$_2$ at all time points.

| Biodistribution of Tc-99m LL2-F(ab')₂ in BALB/c Mice % injected dose/gram of tissue ± standard deviation, 3 animals/time-point | | | |
|---|---|---|---|
| Tissue | 1 hr | 4 hr | 24 hr |
| Blood | 39.9 ± 0.97 | 23.7 ± 4.12 | 5.29 ± 0.88 |
| Liver | 9.07 ± 0.27 | 11.1 ± 1.20 | 8.87 ± 0.66 |
| Spleen | 7.64 ± 0.87 | 7.06 ± 1.33 | 7.86 ± 0.89 |
| L. Kidney | 18.4 ± 4.31 | 25.5 ± 6.16 | 29.2 ± 1.8 |
| Stomach | 7.14 ± 0.79 | 5.48 ± 0.16 | 1.28 ± 0.61 |
| Muscle | 0.85 ± 0.31 | 0.92 ± 0.11 | 0.83 ± 0.11 |
| Lungs | 9.35 ± 1.70 | 6.84 ± 1.06 | 3.29 ± 0.67 |
| Urine | 82.1 ± 28.8 | 19.3 ± 15.2 | 3.64 ± 0.13 |
| Small Int. | 5.61 ± 0.36 | 6.28 ± 3.86 | 1.88 ± 0.14 |
| Large Int. | 1.51 ± 0.24 | 9.17 ± 0.73 | 1.67 ± 0.36 |

Example 3

Comparison of TC-99m-IMP 155-LL2 F(ab')₂ and I-125 Labeled LL2 F(ab')₂ in Ramos Tumor Bearing Nude Mice Tc-99m Labeling An IMP 155-LL2-F(ab')₂ kit was labeled with 5 mCi 99m-TcO₄; in 0.3 mL saline. The kit was incubated for 30 mm at room temperature then diluted to 0.75 mL with saline and purified through two successive 3 mL pH 5.3 acetate buffered saline Sephadex G50–80 spin columns.

I-125 Labeling

The antibody fragment LL2-F(ab')₂, 23.3 μL (5.15 mg/mL) was mixed with 50 μL 0.5 M, pH 7.5, phosphate buffer and added to a vial containing 2.5 mCi I-125. A solution of chloramine-T, 12 μL (0.0034 g in 2 mL PBS) was added and the reaction was allowed to proceed for 3 min at room temperature before it was quenched with 20 μL (0.0254 g in 10 mL) of a solution of sodium metabisulfite.

Mixed Label

The I-125 LL2-F(ab')₂ was in a solution which contained 1.6 mCi in ~3 mL. The I-125 LL2-F(ab')2 and the Tc-99 m LL2 F(ab')₂were mixed in a ratio of 5 μCi I-125 to 25 μCi Tc-99m. The final mixed solution contained 220 μCi I-125 LL2-F(ab')₂ and 1.04 mCi Tc-99m IMP 155-LL2-F(ab')₂ in 2.0 mL of solution.

Biodistribution

A group of five Ramos tumor-bearing nude mice with similar sized tumors were used per time-point. Each animal was injected with 50 μL of the premixed solution (5 μCi I-125 and 25 μCi Tc-99m). The animals were anesthetized and sacrificed by cervical dislocation at 1 hr, 4 hr, and 24 hr. The following tissues and organs were collected and counted: Tumor, Blood, Muscle, Liver, Kidneys, Spleen, Stomach.

| Tissue | 1 hr | Ratio | 4 hr | Ratio | 24 hr | Ratio |
|---|---|---|---|---|---|---|
| Tc-99m-IMP 155-LL2-F(ab')₂ Conjugate Co-injected With I-125-LL2-F(ab')₂ Selected Tc-99m Biodistribution Results % ID/g ± SD, 5 Animals/Time Point | | | | | | |
| Ramos | 3.39 ± 0.84 | | 2.94 ± 0.81 | | 9.56 ± 2.83 | |
| Blood | 18.4 ± 2.7 | 0.19 | 11.57 ± 1.86 | 0.26 | 2.60 ± 0.392 | 3.71 |
| Liver | 6.80 ± 0.52 | 0.50 | 4.42 ± 0.60 | 0.68 | 6.21 ± 0.432 | 1.54 |
| Spleen | 3.98 ± 0.47 | 0.83 | 4.04 ± 0.69 | 0.74 | 3.84 ± 0.774 | 2.51 |
| L. Kidney | 11.86 ± 1.56 | 0.29 | 10.87 ± 1.84 | 0.28 | 19.05 ± 4.00 | 0.51 |
| Stomach | 1.71 ± 0.75 | 2.13 | 2.02 ± 1.90 | 2.24 | 1.92 ± 2.43 | 9.30 |
| Muscle | 0.91 ± 0.22 | 3.83 | 0.77 ± 0.166 | 3.86 | 0.78 ± 0.16 | 12.6 |
| Tc-99m IMP 155-LL2 F(ab')₂ Conjugate Coinjected With I-125 LL2 F(ab')₂ Selected I-125 Biodistribution Results % ID/g ± SD | | | | | | |
| Ramos | 3.63 ± 0.94 | | 3.48 ± 0.81 | | 4.22 ± 1.02 | |
| Blood | 18.4 ± 2.2 | 0.20 | 12.7 ± 1.55 | 0.28 | 1.99 ± 0.30 | 2.12 |
| Liver | 2.50 ± 1.397 | 0.50 | 2.96 ± 0.31 | 1.20 | 0.49 ± 0.04 | 8.64 |
| Spleen | 4.38 ± 0.43 | 0.83 | 4.13 ± 0.52 | 0.85 | 0.83 ± 0.10 | 5.08 |
| L. Kidney | 12.89 ± 1.06 | 0.28 | 7.62 ± 1.16 | 0.47 | 1.06 ± 0.27 | 4.14 |
| Stomach | 5.71 ± 1.87 | 0.65 | 5.41 ± 0.66 | 0.65 | 3.17 ± 0.82 | 1.38 |
| Muscle | 1.10 ± 0.24 | 3.35 | 0.97 ± 0.19 | 3.63 | 0.30 ± 0.04 | 14.1 |

Example 4

Comparison of TC-99m IMP 155-LL2-F(ab')₂ to TC-99m LL2 Fab'

Tc-99m Labeling of IMP 155-LL2-F(ab')₂ Conjugate

An IMP 155-LL2-F(ab')₂ kit was labeled with 5 mCi 99m-TcO₄⁻ in 0.3 mL saline. The kit was incubated for 30 mm at room temperature then diluted to 0.75 mL with saline and purified through two successive 3 mL pH 5.3 acetate buffered saline Sephadex G 50–80 spin columns. Diluted sample to 500 μCi/mL with saline.

Tc-99m LL2-Fab' Labeling:

An LL2-Fab' kit (LYMPHOSCAN™-Immunomedics, Inc., Morris Plains, N.J.) was radiolabeled at room temperature with 31 mCi Tc-99m in 1 mL added to the lyophilized kit. A 50-μL aliquot (1.55 mCi) was removed and diluted with saline to 3 mL (500 μCi/mL).

Biodistribution

A group of 5 Ramos tumor bearing nude mice with similar sized tumors were used per time point. Each animal was injected with 50 μL of the labeled antibody fragment (25 μCi Tc-99m). The animals were anesthetized and sacrificed by cervical dislocation at 4 hr and 24 hr. The following tissues and organs were collected and counted: Tumor, Blood, Muscle, Liver, Kidneys, Spleen, Stomach. The ratio of tumor-to-normal organ is given for each organ.

| Comparison of Tc-99m IMP 155-LL2-F(ab')₂ Conjugate With Tc-99m LL2 Fab' | | | | |
|---|---|---|---|---|
| Tissue | 4 hr | Ratio | 24 hr | Ratio |
| Tc-99m IMP 155-LL2-F(ab')₂ Conjugate Biodistribution | | | | |
| Ramos | 3.75 ± 0.45 | | 8.32 ± 2.77 | |
| Blood | 14.6 ± 0.99 | 0.26 | 1.64 ± 0.26 | 4.97 |
| Liver | 6.28 ± 0.44 | 0.60 | 6.72 ± 1.08 | 1.22 |
| Spleen | 4.39 ± 0.70 | 0.87 | 2.57 ± 0.46 | 3.18 |
| L. Kidney | 15.5 ± 1.14 | 0.24 | 17.5 ± 3.87 | 0.48 |
| Stomach | 1.2 ± 0.4 | 3.47 | 0.64 ± 0.11 | 13.0 |
| Muscle | 0.79 ± 0.18 | 4.92 | 0.57 ± 0.11 | 14.5 |

-continued

Comparison of Tc-99m IMP 155-LL2-F(ab')₂ Conjugate
With Tc-99m LL2 Fab'

| Tissue | 4 hr | Ratio | 24 hr | Ratio |
|---|---|---|---|---|
| Tc-99m LL2-Fab' Biodistribution | | | | |
| Ramos | 3.73 ± 0.89 | | 2.09 ± 0.73 | |
| Blood | 3.52 ± 1.02 | 1.13 | 0.32 ± 0.04 | 6.67 |
| Liver | 3.69 ± 0.40 | 1.02 | 1.48 ± 0.23 | 1.38 |
| Spleen | 1.93 ± 0.21 | 1.95 | 0.79 ± 0.13 | 2.58 |
| L. Kidney | 75.5 ± 11.1 | 0.05 | 23.7 ± 4.99 | 0.09 |
| Stomach | 0.90 ± 0.24 | 4.30 | 0.31 ± 0.07 | 6.88 |
| Muscle | 0.61 ± 0.04 | 6.14 | 0.26 ± 0.04 | 7.95 |

Example 5

In Vitro Stability Studies

The stability of the Tc-99m labeled conjugates was screened by labeling the conjugates by exchange with Tc-99m-glucoheptonate followed by purification of the labeled protein through two successive Sephadex G 50–80 gel columns which removed all of the unbound small molecular weight Tc-99m species. The purified material was then analyzed by ITLC (0.1 M citrate, pH 5), size exclusion HPLC and reverse phase HPLC.

The stability of the different conjugates was assessed by incubation in the gel filtration buffer or labeling buffer at room temperature over 24 hr, by challenge with 1 mM cysteine at 37° C. over 24 hr and by incubation in serum at 37° C. over 24 hr.

Analytical Methods

ITLC

ITLC strips were spotted with an aliquot (0.2 μCi) of the labeled solution and eluted with pH 5, 0.1 M citrate buffer. The labeled protein remained at the origin while 99m-TcO₄⁻, and Tc-99m-glucoheptonate were eluted up the strip.

Size Exclusion HPLC

A Bio-Rad, Bio-Sil SEC 250, gel filtration HPLC column (300 mm×7.8 mm) was eluted at 1 mL/min with a pH 6.8, 0.2 M phosphate buffer containing 0.02% sodium azide.

Analysis of Tc-99m Labeled Species by
Size-Exclusion Chromatography

| Retention Time | Tc-99m Labeled Species |
|---|---|
| 8 min | Aggregate |
| 9–10 min | Tc-99m-Peptide Conjugate-LL2 F(ab')₂ |
| 11 min | Tc-99m-Peptide Conjugate-LL2 Fab' |
| 13–16 min | Tc-99m Small MW species: peptides, glucoheptonate, phosphate etc. |
| 16 min | 99m-TcO₄⁻ |

Reverse-Phase HPLC

Reverse Phase HPLC was performed on a Waters Radial-Pak, C-18, Nova-Pak (4 μ, 100×8 mm) column. The column was eluted with a gradient using two buffers (Buffer A, 0.1% aqueous TFA, Buffer B 90% acetonitrile, 10% water, 0.1% TFA). The gradient was as follows: Flow Rate 3 mL/min 100% Buffer A to 100% Buffer B over 10 min, flow rate 5 mL/min for 5 min. The reverse-phase HPLC method was useful for identifying the nature of the Tc-99m labeled small molecular weight species. The stable, Tc-99m labeled proteins did not elute well on reverse-phase HPLC.

Reverse-Phase HPLC Analysis of Tc-99m Labeled Species

| Retention Time | Tc-99m Labeled Species |
|---|---|
| Void Volume 1–1.5 min | 99m-TcO₄⁻, and 99m-Tc-glucoheptonate |
| 5–8 min sharp peaks | Tc-99m labeled peptides |
| 5–11 min broad lumps | Tc-99m labeled protein |

Tc-99m-IMP 126-LL2-F(ab')₂

The crude labeled protein, prepared analogously to labeled IMP-155-LL2-F(ab')₂, was purified on a Sephadex G 50–80 gel column in pH 7.3, 0.1 M phosphate buffer. An aliquot was removed and diluted five-fold in saline. The saline solution was incubated for 1 hr at 37° C. Size-exclusion HPLC analysis showed that approximately 5% of the activity was dissociated from the protein after 1 hr.

Incubation of Tc-99m-IMP 126-LL2-F(ab')₂ in pH 7.3, 0.1 M phospate buffer containing 1 mM cysteine at 37° C. for 1.5 hr caused 31% of the labeled protein to be reduced to the Tc-99m IMP 126-Fab' fragment. There was 56% of the Tc-99m-IMP 126-LL2-F(ab')₂ left intact and 12% of the activity was converted to low molecular weight species such as Tc-99m cysteine.

Incubation of Tc-99m-IMP 126-LL2-F(ab)₂ diluted tenfold in fresh human serum at 37° C. for 21 hr caused 34% of the activity to be lost as low molecular weight species. There were three Tc-99m labeled protein species all about the same percentage (20%) of the activity. The peaks appeared to be due to aggregate, Tc-99m-IMP 126-LL2-F(ab')₂, and Tc-99m-IMP 126-LL2 Fab'.

Tc-99m-IMP 140-LL2-F(ab')₂

The labeled peptide, prepared analogously to labeled IMP-155-LL2-F(ab')₂, was purified and stored in pH 7.3, 0.1 M phosphate buffer over night. Size-exclusion HPLC analysis showed that approximately 30% of the activity was dissociated from the protein after 24 hr. Reverse phase HPLC analysis indicated that the bulk of the Tc-99m labeled small molecular weight species was present as the Tc-99m labeled peptide that had hydrolyzed off the protein. The conclusion was that the acylhydrazone linkage to the antibody was unstable.

Tc-99m-IMP 155-LL2-F(ab')₂

The labeled peptide was purified and stored in pH 7.3, 0.1 M phosphate buffer over night. Size exclusion HPLC analysis showed less than 5% decomposition to small molecular weight species after incubation for 24 hr at room temperature.

Incubation of Tc-99m-IMP 155-LL2-F(ab')₂ in pH 7.3, 0.1 M phospate buffer containing 1 mM cysteine at 37° C. caused the bulk of the labeled protein (61.5%) to be reduced to the Tc-99m IMP 155-Fab' fragment. There was 8% of the Tc-99m-IMP 155-LL2 F(ab')₂ left intact and 30% of the activity was converted to low molecular weight species such as Tc-99m cysteine.

Incubation of Tc-99m-IMP 155-LL2-F(ab')₂ diluted tenfold in fresh human serum at 37° C. for 21 hr caused 10% of the activity to be lost as low molecular weight species. There were three Tc-99m labeled protein species. The peaks appeared to be due to aggregate (38%), Tc-99m-IMP 155-LL2-F(ab')₂ (42%), and Tc-99m-IMP 155-LL2-Fab' (9%). The aggregate formation may be an artifact due to disulfide formation caused by exposure to oxygen.

Example 6

Aggregate Formation

Some protein aggregate (2–10%) formed during the conjugation process as was shown by a higher molecular weight peak present in the UV and Tc-99m labeling of the protein when analyzed by size exclusion HPLC. The aggregate appeared to be due to disulfide formation between the peptide thiols of one conjugate with the thiols of another conjugate. The aggregate disappeared on treatment with excess cysteine. Some aggregate formation was observed in serum during in vitro stability studies. This also appeared to be due to disulfide formation. Fresh serum showed less aggregation than aged serum and addition of cysteine to the serum greatly reduced the amount of aggregate that was formed. The in vivo serum samples showed some aggregate formation but the bulk of the activity was present as the Tc-99m-IMP 155-LL2 F(ab')$_2$.

Example 7

Peptide Loading on Oxidized LL2-F(ab')$_2$

The conjugations of IMP 155 were carried out as described above and the antibody concentration was measured by the UV absorbance of an aliquot at 280 nm. The thiol content was measured using an Ellman's assay and the thiol concentration in the aliquot was correlated to the antibody content as measured by UV to obtain the thiol loading on the antibody. It was later determined that the UV measurement method was inaccurate because the peptide has a significant absorbance at the wave length used to determine the protein content thus giving an artificially high number for the protein content. The analysis was then switched to matrix assisted laser desorption ionization (MALDI) mass spectrometry to unambiguously determine the number of peptides attached to the protein. The results in the tables below show that the peptide loading was consistent over a range of peptide to antibody ratios used during the conjugation. Using the oxidation and conjugation conditions described above there are added, on average, 4 peptides per antibody.

Conjugation of IMP 155 to Periodate Oxidized LL2 F(ab')$_2$

| Expt. No. | Peptide/ab Ratio | Thiol Loading/ab | Notes |
|---|---|---|---|
| 1 | 100 | 2.1, 2.4 | Two conjugations |
| 2 | 100 | 2.6 | 3.8 pep/ab MALDI MS |
| 3 | 100 | 2.3 | |
| 4 | 50 | 2.5, 2.7 | Two fractions |
| 5 | 100 | 2.7 | Same batch OxLL2 |
| 6 | 50 | 2.3 | 4.3 pep/ab MALDI MS |
| 7 | 52 | 3.1 | 100 µg Tin in conjugation |
| 8 | 10 | 1.8 | |

Mass Spectrometry Data

| Expt. No. | Sample | MW+ MALDI | Difference | Peptides/ab |
|---|---|---|---|---|
| NA | LL2 F(ab')$_2$ | 103514 | | |
| NA | Oxidized LL2 F(ab')2 | 103168 | | |
| 6 | IMP 155-LL2 F(ab')$_2$ 5Oxpep | 106643 | 3475 | 4.3 |
| 2 | IMP 155-LL2 F(ab')$_2$ 100xpep | 106240 | 3072 | 3.8 |
| NA | IMP 155 | 808 (ESMS) | | |

Example 8

Control Experiments

Conjugation Control

A conjugation control experiment was carried to determine if the free thiol containing peptide was reacting with disulfides on the antibody to generate protein thiols or if the peptide was attached to the antibody by some means other than to the oxidized carbohydrate. In this experiment unoxidized LL2-F(ab')$_2$ was treated with 50 fold excess IMP 155 at the same time as a lot of periodate oxidized LL2 F(ab')$_2$. The periodate oxidized LL2-F(ab')$_2$ formed a conjugate which contained 2.3 thiols/ab as determined by UV (4.3 peptides/ab by MALDI) and the unoxidized LL2-F(ab')$_2$ contained 0.2 thiols/ab as determined by UV. This experiment demonstrated that periodate oxidation was necessary in order to add the peptide to the antibody and that the thiols present were on the peptide and not a product of disulfide interchange.

Tc-99m Labeling Control

A control experiment was carried out in which a batch of LL2-F(ab')$_2$ was treated with periodate and conjugated as described above with 100 fold excess of the peptide IMP 140 except that 10 mg/mL sodium cyanoborohydride was added after two hours of conjugation and the conjugation was continued for two hours more before purification. The control batch of the LL2-F(ab')$_2$ was treated the same except there was no periodate present in the oxidation control. The two antibody preparations were labeled by exchange with Tc-99m-glucoheptonate. The portion that was treated with periodate before the conjugation produced a 60% labeling yield as shown by ITLC in 0.1 M, pH 5 citrate buffer and the unoxidized control showed 6% of the Tc-99m was bound to the protein according to the ITLC.

In addition, IMP 171, a peptide which contains two metal binding ligands, was conjugated to LL2-F(ab')$_2$ using the same process as described for IMP-155. It was necessary to use a peptide to antibody ratio of 50:1 or less with this peptide because the increased number of thiols could cause reduction of the LL2-F(ab')$_2$ to the LL2-Fab'. This reaction did produce a conjugate, IMP 171-LL2-F(ab')$_2$ with twice the number of thiols (5.3 thiols/ab) as compared to the IMP 155-LL2-F(ab')$_2$ conjugation (2.3 thiols/ab) carried out on the same batch of oxidized antibody.

IMP-171 H$_2$NHN-CH$_2$CO-D-Asp-D-Lys(TscG-Cys)-D-Asp-D-Lys-D-Lys(TscG-Cys)-D-Asp-D-Lys-NH$_2$ MH+1412

Example 9

Rhenium Labeling

Rhenium labeling using a pre-reduction procedure for the Re-188

These conjugates may be labeled with rhenium isotopes (primarily Re-186 and Re-188), which are then useful for radioimmunotherapy. Because reduction of perrhenate requires more stannous ion (typically above 200 ug/mL final concentration) than is needed for the reduction of technetium, extra care needs to be taken to ensure that the higher levels of stannous ion do not reduce sensitive disulfide bonds such as those present in the hinge region of F(ab')$_2$ fragments. During radiolabeling with rhenium, similar procedures are used as are used with the Tc-99m, except that contact time between MAb and Sn(II) is limited timewise to prevent disulfide bond reductions, or the perrhenate rhenium is reduced prior to mixing with antibody fragment conjugate. An aqueous solution of the thiol ligand containing substrate is then mixed with $^{188}$ReOCl$_3$(PPh$_3$)$_2$ in CH$_2$Cl$_2$ by the method of Lisic et. al. The CH$_2$Cl$_2$ is then removed under a stream of nitrogen and dissolved in 0.1 mL of a 10% aqueous solution of 2-hydroxypropyl-β-cyclodextrin (HPCD). The HPCD solution is then mixed with 0.5 mL of a solution of the IMP-155-LL2 F(ab')$_2$ (4 mg/mL) which is incubated at room temperature for 30 min.

Example 10

Technetium Labeling
Tc-99m Labeling of a Thiol-containing Octreotide
IMP 162 GD$_d$DK(TscGC)F$_d$CFW$_d$KTCTol MH$^+$ 1667

The peptide, IMP 162 (0.0012 g) was dissolved in 30 mL of an aqueous solution containing 10% HPCD, 200 mM glucoheptonate, 14 mM sodium acetate, and 12 mM ascorbic acid at pH 5.29. A stannous solution was prepared by mixing 0.2 mL of 200 mg/mL SnCl$_2$ in 6 M HCl with 3.8 mL of the HPCD glucoheptonate solution. A 0.2 mL aliquot of the stannous/HPCD solution was added to the peptide solution and the solution was then filtered through a 0.22 μm Millex GV filter in 1.5 mL aliquots into lyophilization vials. The vials were then frozen, lyophilized and sealed under vacuum.

Tc-99m Kit Labeling

The lyophilized kit was reconstituted with 20 mCi $^{99m}$TcO$_4^-$ in 1.5 mL saline and incubated at room temperature for 10 min and then heated in a boiling water bath for 15 min. Labeling is complete and quantitative.

Example 11

Drug Conjugate
Conjugation of a Chemotherapy Drug to a Disulfide-containing Peptide An analog of octreotide having an appended N-terminal serine residue attached to the original octapeptide is oxidized using sodium m-periodate to generate an N-terminal aldehyde. This intermediate is reacted with an amount of IMP-155 peptide sufficient to convert all aldehyde groups present on the serine-octreotide to N-terminal hydrazones. The hydrazones are reduced to alkyl hydrazines using sodium cynanoborohydride, and the intermediate thiol-appended IMP-155-hydrazinyl-octreotide is purified and coupled with the anti-cancer drug calicheamicin via thiol exchange with the trisulfide group of the latter. The product calicheamicin-octreotide is comprised of a disulfide-IMP 155-peptidyl-hydrazine linker.

Example 12

Drug Conjugate
Site-specific Substitution of Doxorubicin onto a Disulfide Bond-containing Polypeptide a) Preparation of an Aldehyde-containing (scFv)$_2$ fragment A solution of a human (scFv)$_2$ fragment bearing an N-terminal serine amino-acid, at 3 mg/mL, is treated with 10 mM sodium periodate for 2 h in the dark at 4° C. Glycerol is added to a 20 mM final concentration, to destroy excess periodate, and the reaction stirred for a further 20 minutes. The N-terminal oxidized (scFv)$_2$ is purified from low molecular weight contaminants on a column of G-10-Sephadex equilibrated and run in argon-degassed 0.1 M sodium acetate, pH 5.5, containing 1 mM EDTA. The product is concentrated to 5 mg/mL prior to further reaction.

b) Preparation of a Thiol-appended (scFv)$_2$ Fragment

The N-terminal aldehyde-(scFv)$_2$ intermediate, obtained as in a), is treated with a freshly-prepared DMSO solution of p-(2-thioethyl)-phenylhydrazine (TEPH) at a molar excess of 20:1, and the reaction is stirred for 2 h at 4° C. The product, TEPH-(scFV)$_2$, containing a hydrazone bond, is obtained by purification on a column of G-10-Sephadex equilibrated and run in argon-degassed 0.1 M sodium acetate, pH 6.5, containing 1 mM EDTA. Optionally, prior to purification, the phenylhydrazone is reduced to a phenylhydrazine linkage by a 2 h reaction in the presence of 10 mM sodium borohydride, after pH adjustment of the initial reaction mixture from 5.5 to 7.0 with a small amount of sodium carbonate. The product TEPH-(scFv)$_2$ is analyzed by SE-HPLC on a Bio-Sil GF-125 column equilibrated in 0.5 M sodium phosphate, pH 6.5, to confirm the lack of breakdown into scFv monomers. Aliquots of the product are also separately analyzed for protein concentration by the bicinchoninic acid (BCA) method, and for thiol content by the Ellman reaction, and thus by deduction is determined the number of thiol groups per mole of TEPH-(scFv)$_2$.

c) Activation of Doxorubicin to Maleimido-doxorubicin

A solution of doxorubicin hydrochloride (10 mM) in 5 mL of 50% DMSO/0.1 M sodium borate buffer, pH 8.3, is treated with a two-fold molar excess of the commercially-available cross-linker m-maleimidobenzoyl-N-hydroxysuccinimide ester (MBS, Pierce Chem. Co., Rockford, Ill.). The reaction mixture is allowed to stir for 3 h at room temperature, before being diluted to 20 mL with 5% sodium chloride solution. The mixture is extracted with 3×20 mL of a substantially water-immiscible organic solvent such as ethyl acetate, and the combined organic extracts washed with 3 ×20 mL 0.1 M sodium bicarbonate, pH 8.0. The organic solution is dried over anhydrous sodium sulfate, filtered, and evaporated to obtain the maleimido-doxorubicin.

d) Coupling of Maleimido-doxorubicin to TEPH-(scFv)$_2$

TEPH-(scFv)$_2$ in argon-degassed 0.1 M sodium acetate, pH 6.5, containing 1 mM EDTA, at 4° C., is made 15% in DMSO, and treated with a 2×molar excess (to thiol content) of maleimido-doxorubicin in DMSO, added in one portion with rapid stirring. Stirring is continued for 1 h at 4° C., and the doxorubicin-(scFv)$_2$ is purified by column chromatography on a Sephadex G-10 gel column equilibrated in 0.2 M sodium phosphate buffered 0.9% sodium chloride, pH 7.5.

It will be appreciated by those of skill in the art that many other species may be substituted for those exemplified and illustrated herein without departing from the spirit and scope of the present invention.

What is claimed is:

1. A method of producing a diagnostic or therapeutic conjugate or chelator precursor thereof, comprising contacting a protein, polypeptide or peptide containing at least one disulfide bond which is necessary to maintain its biological activity, and also containing an aldehyde or ketone group, with a thiol-hydrazine-containing diagnostic or therapeutic agent or chelator precursor thereof, wherein said thiol is unprotected before, during and after said contacting, and optionally reducing the resultant hydrazone to a hydrazine, to form a stable diagnostic or therapeutic conjugate of said protein, polypeptide or peptide or chelator precursor thereof.

2. The method of claim 1, wherein said thiol-hydrazine-containing diagnostic or therapeutic agent has the formula HS-Q-NHNH$_2$, wherein Q is a linking moiety selected from the group consisting of alkyl groups, aryl groups, cycloalkyl groups, peptides, and combinations thereof, said linking moiety further comprising a diagnostic or therapeutic moiety or chelator precursor thereof.

3. The method of claim 1, wherein said diagnostic or therapeutic agent is selected from the group consisting of drugs, antibodies, antibody fragments, proteins, glycoproteins, DNA, RNA, PNA, metal complexes, diagnostic and therapeutic radiolabeled species, enzymes, toxins and sugars.

4. The method of claim 1, wherein said therapeutic agent is a drug derivative comprising a thiol-binding linker.

5. The method of claim 1, wherein said peptide comprises D-amino acids.

6. A diagnostic or therapeutic conjugate of a protein, polypeptide or peptide containing at least one disulfide bond which is necessary to maintain its biological activity, produced by the method of claim 1.

7. The method of claim 1, wherein said conjugate comprises a chelator precursor, and wherein said method further comprises adding a diagnostic or therapeutic cation to said chelator thereby forming said diagnostic or therapeutic conjugate.

8. The method of claim 1, wherein said thiol-hydrazine-containing diagnostic or therapeutic agent comprises a chelator.

9. The method of claim 8, wherein said thiol-containing chelator is a thiosemicarbazonylglyoxlcysteine.

10. The method of claim 1, wherein said diagnostic or therapeutic agent is a thiol-binding cationic radioisotope.

11. The method of claim 10, wherein said cationic radioisotope is generated in situ.

12. The method of claim 10, wherein said diagnostic or therapeutic radioisotope is a radioisotope of an element selected from the group consisting of technetium, rhenium, zinc, copper, mercury, cadmium, platinum, palladium, lead and bismuth.

13. The method of claim 12, wherein said radioisotope is Tc-99m, Re-186 or Re-188.

14. The method of claim 1, wherein said protein is a glycosylated divalent antibody fragment whose partially oxidized carbohydrate portion is joined through a hydrazone or hydrazine linkage to a thiol-containing moiety.

15. The method of claim 14, wherein said divalent antibody fragment is a F(ab')$_2$ or F(ab)$_2$ fragment.

16. The method of claim 14, wherein said thiol-containing moiety comprises a chelator.

17. The method of claim 16, wherein said partially oxidized carbohydrate portion is joined to said chelator by:

oxidizing the carbohydrate portion of a glycosylated divalent antibody fragment to generate aldehyde and ketone groups; and reacting the aldehyde and ketone groups on the oxidized fragment with a peptide comprising one or more thiol-containing chelators and bearing an alkylhydrazine group, and optionally reducing the resultant hydrazone to a hydrazine.

18. The method of claim 17, wherein said peptide comprising said thiol-containing chelator is H$_2$NHN-CH$_2$-CO-D-Asp-D-Lys(TscG-Cys-)-D-Asp-D-Lys-NH$_2$, wherein TscG is thiosemicarbazonylglyoxyl, said peptide being joined by a hydrazone or hydrazine linkage to the partially oxidized carbohydrate portion of said glycosylated divalent antibody fragment.

19. A kit for producing a diagnostic or therapeutic conjugate produced by the method of claim 1 which comprises:

a protein, polypeptide or peptide containing at least one disulfide bond which is necessary to maintain its biological activity, and bearing at least one thiol-containing moiety comprising a chelator linked thereto through a hydrazone or hydrazine linkage; and a thiol-reactive diagnostic or therapeutic cationic radionuclide, either preformed or generated in situ.

20. A kit of claim 19, for use in producing a radiolabeled glycosylated divalent antibody fragment, comprising a glycosylated divalent antibody fragment whose partially oxidized carbohydrate portion is joined through a hydrazone or hydrazine linkage to a peptide comprising at least one thiol-containing chelator.

21. The kit of claim 20, wherein said thiol-containing chelator is a thiosemicarbazonylglyoxlcysteine.

22. The kit of claim 20, wherein said divalent antibody fragment is a F(ab')$_2$ or F(ab)$_2$ fragment.

23. The kit of claim 20, which further comprises stannous ions for reducing radiopertechnetate or radioperrhenate anions to generate cationic technetium or rhenium radioisotopes in situ.

24. The kit of claim 20, wherein said peptide comprises D-amino acids.

25. The kit of claim 24, wherein said peptide comprising said thiol-containing chelator is H$_2$NHN-CH$_2$-CO-D-Asp-D-Lys(TscG-Cys-)-D-Asp-D-Lys-NH$_2$, wherein TscG is thiosemicarbazonylglyoxyl, said peptide being joined by a hydrazone or hydrazine linkage to the partially oxidized carbohydrate portion of said glycosylated divalent antibody fragment.

* * * * *